(12) United States Patent
Fargahi (10) Patent No.: US 11,166,734 B2
(45) Date of Patent: Nov. 9, 2021

(54) CATHETER DEVICES FOR CHRONIC TOTAL OCCLUSION RECANALISATION

(71) Applicant: BIOTRONIK AG, Buelach (CH)

(72) Inventor: Amir Fargahi, Buelach (CH)

(73) Assignee: BIOTRONIK AG, Buelach (CH)

(*) Notice: Subject to any disclaimer, the term of this patent is extended or adjusted under 35 U.S.C. 154(b) by 134 days.

(21) Appl. No.: 16/385,583

(22) Filed: Apr. 16, 2019

(65) Prior Publication Data

US 2019/0336146 A1 Nov. 7, 2019

(30) Foreign Application Priority Data

May 3, 2018 (EP) .................... 18170549

(51) Int. Cl.
*A61B 17/22* (2006.01)
*A61M 25/10* (2013.01)
*A61B 90/00* (2016.01)

(52) U.S. Cl.
CPC ............ *A61B 17/22* (2013.01); *A61M 25/104* (2013.01); *A61B 2017/22038* (2013.01); *A61B 2017/22094* (2013.01); *A61B 2090/3966* (2016.02); *A61M 2025/1061* (2013.01)

(58) Field of Classification Search
CPC ........ A61M 25/104; A61M 2025/1061; A61M 2025/1079; A61M 2025/1093; A61M 25/1011; A61M 25/1002; A61B 17/22; A61B 2090/3966; A61B 2017/22038; A61B 2017/22094; A61B 2017/22044; A61B 2017/22054; A61B 2017/22069

See application file for complete search history.

(56) References Cited

U.S. PATENT DOCUMENTS

| | | | | |
|---|---|---|---|---|
| 4,990,139 A | * | 2/1991 | Jang | A61M 25/1011 604/101.01 |
| 7,001,420 B2 | * | 2/2006 | Speck | A61M 25/005 604/103.09 |
| 2002/0072706 A1 | * | 6/2002 | Hiblar | A61M 25/0084 604/101.01 |
| 2003/0127158 A1 | * | 7/2003 | Abrams | C22C 14/00 148/402 |
| 2005/0102020 A1 | * | 5/2005 | Grayzel | A61F 2/958 623/1.11 |
| 2006/0271090 A1 | * | 11/2006 | Shaked | A61B 17/12136 606/192 |
| 2007/0250169 A1 | * | 10/2007 | Lang | A61B 17/158 623/17.12 |

FOREIGN PATENT DOCUMENTS

| | | |
|---|---|---|
| WO | 1995016487 A1 | 6/1995 |
| WO | 1999007354 A3 | 2/1999 |
| WO | 2007100365 A1 | 9/2007 |

OTHER PUBLICATIONS

Przykutta, Andreas; European Search Report for Application No. 18170549.2; dated Oct. 31, 2018.

* cited by examiner

*Primary Examiner* — Richard G Louis
(74) *Attorney, Agent, or Firm* — Greer, Burns & Crain, Ltd.; Steven P. Fallon (57) ABSTRACT

A catheter device for the recanalisation of an occlusion in a vessel. A proximal balloon is arranged at the distal end portion of a catheter shaft for anchoring the catheter shaft in the vessel and for opening the occlusion. A distal balloon arranged at the distal end portion for opening the occlusion.

16 Claims, 6 Drawing Sheets

CATHETER DEVICES FOR CHRONIC TOTAL OCCLUSION RECANALISATION

PRIORITY CLAIM

This application claims priority under 35 U.S.C. § 119 and all applicable statutes and treaties from prior European Application EP 18170549.2, filed May 3, 2018.

FIELD OF THE INVENTION

The invention relates to a catheter device for recanalisation of an occlusion in a vessel.

BACKGROUND

Catheter devices of this kind are used in particular for the recanalisation or reopening of a chronic, substantially total occlusion (chronic total occlusion (CTO)) of a vessel in a patient.

CTO interventions of this kind are used in approximately 20% of all patients in a cardiac catheter lab. An average duration of the intervention is approximately between 2 and 2.5 hours. More guide wires, balloon catheters and stents are routinely employed during CRP than in the case of typical percutaneous coronary interventions (PCIs).

For the treatment or recanalisation of chronic total occlusions (CTOs), a catheter device is described in Rowe et al., WO2007/100365A1, entitled Balloon Catheter. That publication describes two balloons arranged one after the other, through which a guide wire extends and is used to position the two balloons in front of the occlusion, wherein the guide wire is guided through the occlusion first.

In systems of this kind, the guide wire lumen provided to receive the guide wire in the two balloons can prove to be disadvantageous, since for this purpose a suitable installation space must be provided, and therefore the device has a relatively large diameter in the region of the balloons.

Furthermore, rebound effects during the balloon inflation are routinely encountered in balloon systems of this kind, since the leading (distal balloon) increases in diameter as it unfolds/dilates and therefore tends to be pushed out from the constricted position.

SUMMARY OF THE INVENTION

A preferred catheter device for recanalisation of an occlusion in a vessel includes a catheter shaft extending along a longitudinal axis having a distal end portion. A proximal balloon is arranged at the distal end portion, the proximal balloon being sized for anchoring the catheter shaft in the vessel and for opening the occlusion, wherein the proximal balloon has a balloon interior into which a fluid medium can be introduced to expand the proximal balloon. A distal balloon is arranged at the distal end portion distally from the proximal balloon, the distal balloon being sized for initially opening the occlusion, wherein the distal balloon has a balloon interior into which a fluid medium can be introduced in order to expand the distal balloon. A guide wire lumen is surrounded by the catheter shaft. A guide wire is configured to be guided in the guide wire lumen. An opening is at the distal end portion of the catheter shaft via which the guide wire can be guided out from the guide wire lumen and from the catheter shaft. The opening is arranged such that the guide wire can extend with a portion of the guide wire outside the distal balloon.

BRIEF DESCRIPTION OF THE DRAWINGS

Further features and advantages of the invention will be explained in the description of drawings of exemplary embodiments of the invention with reference to the drawings, in which.

DETAILED DESCRIPTION OF THE PREFERRED EMBODIMENTS

A preferred catheter device for recanalisation of an occlusion (in particular CTO) in a vessel is proposed, said catheter device includes:

a catheter shaft, which extends along a longitudinal axis and has a distal end portion, a proximal balloon, arranged at the distal end portion, for anchoring the catheter shaft in the vessel and for opening the occlusion, arranged at the distal end portion of the catheter shaft, wherein the proximal balloon has a balloon interior into which a fluid medium can be introduced in order to unfold the proximal balloon, a distal balloon arranged at the distal end portion for opening the occlusion initially, wherein the distal balloon has a balloon interior into which a fluid medium can be introduced in order to unfold the proximal balloon, and a guide wire lumen surrounded by the catheter shaft, and a guide wire that can be guided in the guide wire lumen, wherein the catheter shaft, at the distal end portion, has an opening communicating with the guide wire lumen, via which opening the guide wire can be guided out from the guide wire lumen and from the catheter shaft.

In accordance with the invention it is now provided that the opening is arranged such that the guide wire extends with a portion of the guide wire, guided out from the guide wire lumen via the opening, outside the distal balloon and in particular can be guided past the distal balloon externally, such that the guide wire in particular can be guided past the distal balloon and into the occlusion in order to position the catheter shaft in particular in relation to the occlusion. The guide wire lumen runs through the distal end portion, whereby the guide wire lumen runs within or through the proximal balloon, but does not run through or within the distal balloon.

In accordance with an embodiment it is provided in this regard that the opening is arranged along the longitudinal axis of the catheter shaft between the balloon interior of the proximal balloon and the balloon interior of the distal balloon. In particular, the opening along said longitudinal axis can be provided at the distal end of the proximal balloon or between the distal end of the proximal balloon and a proximal end of the distal balloon. The opening is preferably positioned close to or at the axial center of the proximal balloon. The opening is therefore not located at the periphery or at the outer surface of the proximal balloon. Such a configuration facilitates opening the occlusion not only by the elongate guide element but also by the guide wire via elongation of the guide wire beyond the opening.

If reference is made within the scope of the present invention to a proximal component or a proximal region and a corresponding distal component or a distal region, this means that the distal component or the distal region is distanced further from an operator of the catheter device along the extent of the catheter shaft than the proximal component or the proximal region. The region may be for example an end portion or an end of a component of the catheter device.

On account of the design according to the invention of the catheter device, it is possible to form the distal balloon to be relatively small, since it no longer has to accommodate the guide wire lumen.

The distal balloon in accordance with an embodiment of the invention preferably has a diameter which in the unfolded state of the distal balloon is much smaller than the diameter of the unfolded proximal balloon. The distal balloon is therefore also referred to as a micro balloon. The diameter of the proximal balloon is preferably in particular designed such that the proximal balloon in an unfolded state can lie against the vessel wall of the patient in order to anchor the catheter shaft. In a specific embodiment the diameter of the proximal balloon in its unfolded state is preferably more than twice as big, more preferably more than four times as big and most preferably more than 10-times as big as the diameter of the distal balloon. It is further preferred that the distal balloon is configured to be more rigid than the proximal balloon.

For recanalisation of the CTO, the catheter device or the catheter shaft can be introduced and positioned in the body or the relevant vessel of the patient via the guide wire. The guide wire is then retracted and the distal balloon is guided into the occlusion. The simultaneous dilation of the distal or micro balloon and the proximal balloon forces the occlusion open at the inlet. In further steps, the proximal balloon is deflated, advanced further into the occlusion, and dilated again, until the vessel has been completely opened or the recanalisation of the occlusion is complete.

A CTO recanalisation is simplified by the device according to the invention since the distal balloon is relatively thin and accordingly can be moved more easily into the occlusion. Furthermore, a rebound generated as the distal balloon is dilated can be well intercepted by the proximal balloon, since this can be anchored on the inner wall of the vessel (see above).

It is furthermore provided in accordance with an embodiment of the invention that the catheter device has an elongate guide element, which is formed separately from the guide wire and which protrudes from the second balloon by a distal end portion in the distal direction.

It is furthermore provided in accordance with an embodiment of the invention that the guide element extends through the balloon interior of the distal balloon, wherein the distal end portion of the guide element is guided out from the distal balloon at a distal end of the distal balloon.

In accordance with an embodiment of the invention the guide element can be formed for example by a wire. The wire may have a core that is visible under x-ray and that is formed from platinum or from a platinum alloy, wherein the core can be coated with a cobalt-chromium alloy. Furthermore, the guide element or the wire may have an x-ray marker. Moreover, in one embodiment the elongate guide element is leading from the tip of the distal balloon to the portion guided out from the guide wire lumen in which the guide wire outside the distal balloon distal to the opening of the distal end portion could run.

It is furthermore provided in accordance with the invention that the guide wire lumen of the catheter shaft is surrounded by a wall. Here, it is provided in accordance with an embodiment that the wall of the guide wire lumen extends through the balloon interior of the proximal balloon.

It is furthermore provided in accordance with an embodiment of the invention that the catheter shaft has a shaft lumen surrounded by a wall, via which shaft lumen a fluid medium can be introduced, particularly in simultaneously, into the balloon interior of the proximal balloon and into the balloon interior of the distal balloon in order to unfold the proximal and the distal balloon. Hence, it is provided that the proximal and the distal balloon are inflated with a fluid medium via a single shaft lumen.

It is provided in accordance with an embodiment of the invention that the shaft lumen leads into the balloon interior of the proximal balloon, wherein the balloon interior of the distal balloon is fluidically connected to the shaft lumen via the balloon interior of the proximal balloon.

Such a configuration has the advantage that in the moment the elongate guide element and the distal balloon are to be further introduced into the occlusion, the anchoring in the vessel by the proximal balloon is released, whereby also the distal balloon which shall be introduced into the occlusion decreases its volume and can be forwarded more easily. Therefore, it is not necessary to first release the anchoring of the proximal balloon and tune the volume of the distal balloon thereafter, what would be necessary for a configuration which provides separate shaft lumina for the distal and the proximal balloon.

It is furthermore provided in accordance with an embodiment of the invention that the wall of the shaft lumen extends through the balloon interior of the proximal balloon, wherein the shaft lumen is fluidically connected to the balloon interior of the distal balloon, and wherein the wall of the shaft lumen has at least one lateral outlet opening arranged in the balloon interior of the proximal balloon, via which outlet opening a fluid medium can be introduced into the balloon interior of the proximal balloon in order to unfold the proximal balloon.

It is furthermore provided in accordance with an embodiment that a proximal end portion of the guide element is connected to the wall of the guide wire lumen. This is true in particular for the case in which the lumen does not extend through the balloon interior of the proximal balloon or does not extend therethrough fully as far as the distal balloon.

In accordance with an alternative embodiment of the invention it is provided that the proximal end portion of the guide element is connected to the wall of the shaft lumen. This may be the case in particular if said shaft lumen or the wall of the shaft lumen extends through the balloon interior of the proximal balloon.

It is furthermore provided in accordance with an embodiment of the invention that a proximal end of the distal balloon is connected to the wall of the guide wire lumen and/or to the wall of the shaft lumen.

It is furthermore provided in accordance with an embodiment of the invention that the shaft lumen and the guide wire lumen extend adjacently in the catheter shaft along the longitudinal axis.

In accordance with an alternative embodiment it may likewise be provided that the shaft lumen and the guide wire lumen are arranged coaxially with one another, wherein the guide wire lumen is surrounded by the shaft lumen. In this case the wall of the shaft lumen surrounds the wall of the guide wire lumen.

In accordance with a further embodiment of the invention it is provided that the catheter device has at least one x-ray marker for the proximal balloon, which x-ray marker is arranged in the balloon interior of the proximal balloon on the wall of the guide wire lumen.

Figure 1:
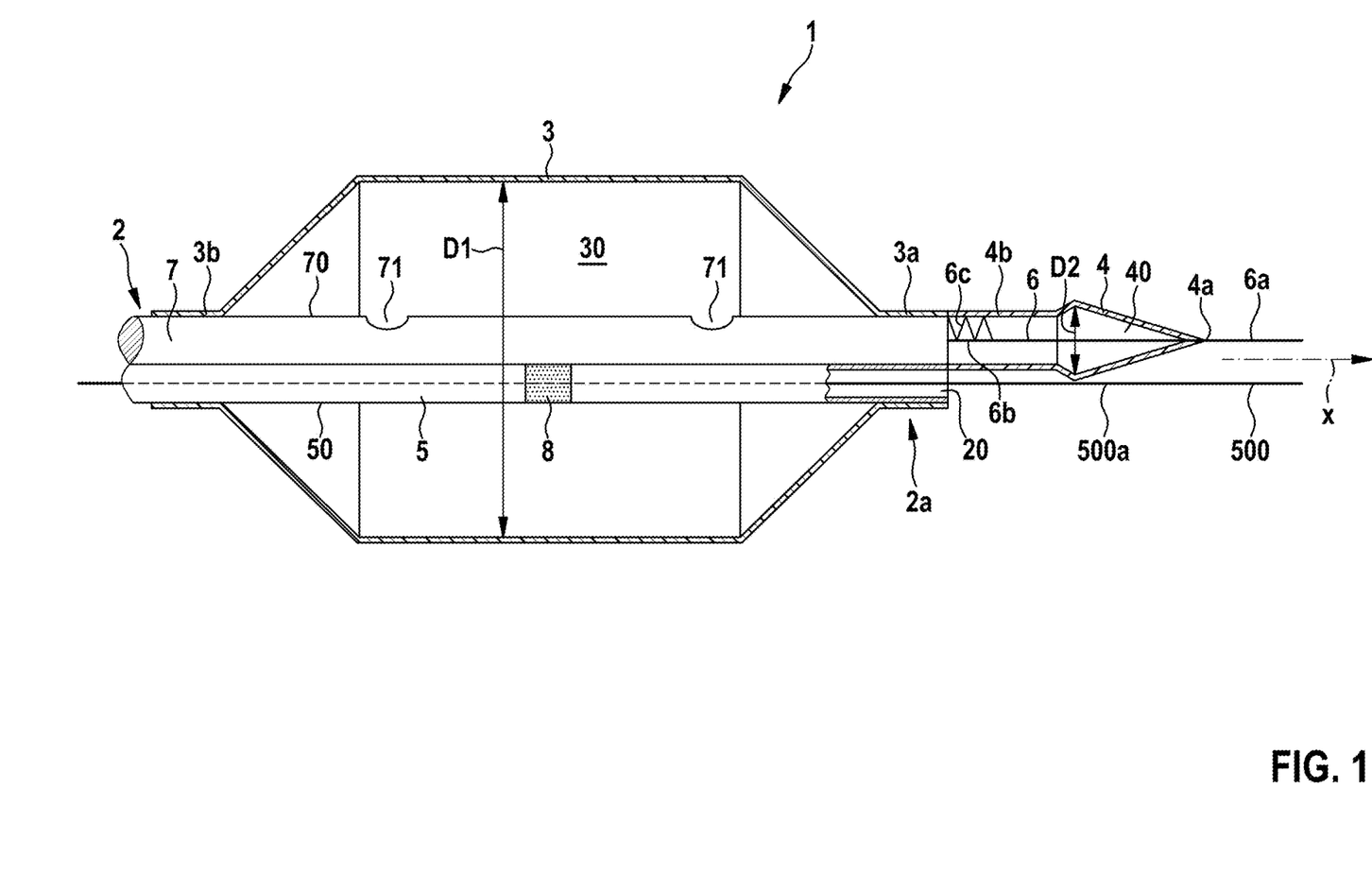
FIG. 1 shows a schematic sectional view of an embodiment of a catheter device according to the invention.
Figure 2:
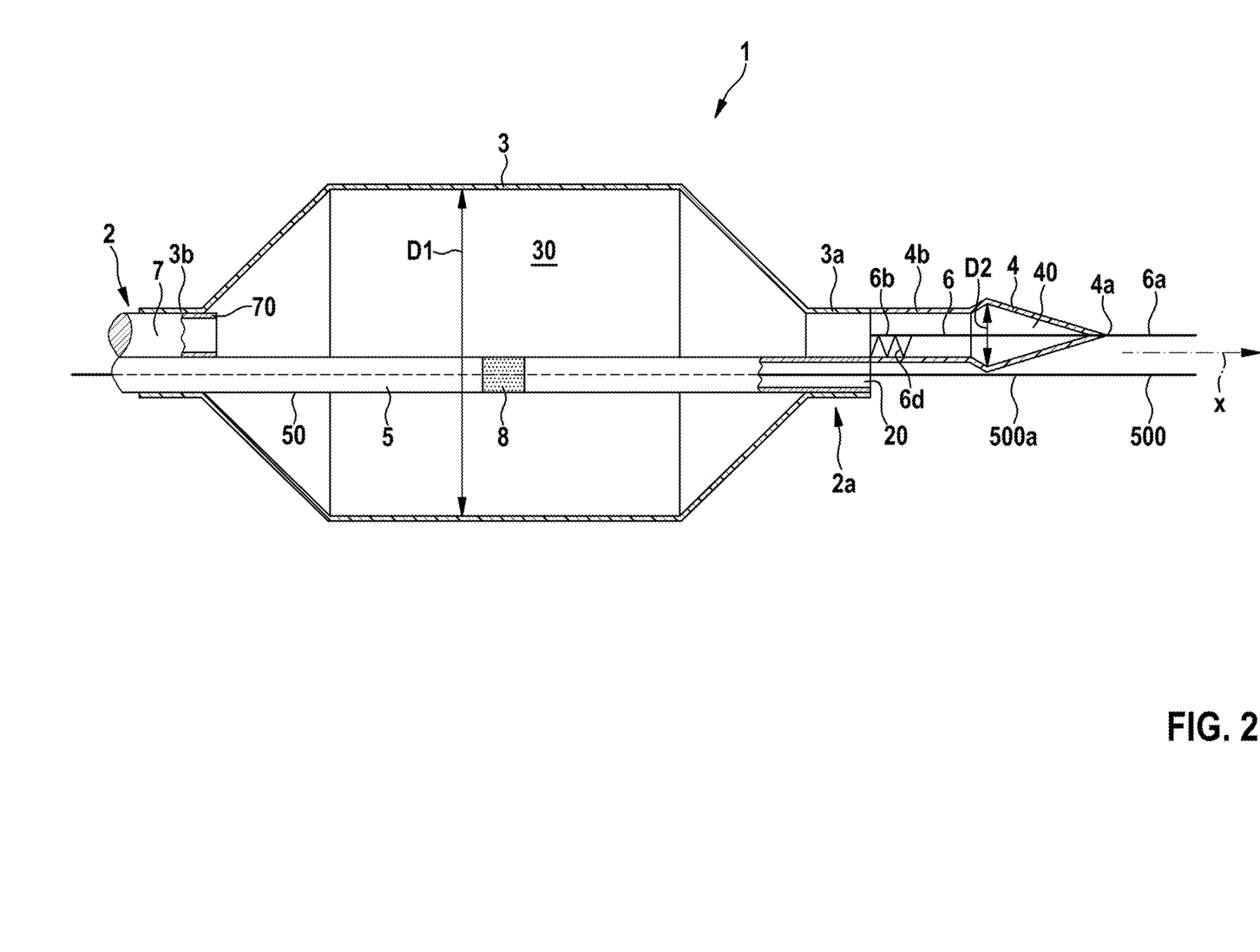
FIG. 2 shows a schematic sectional view of a further embodiment of a catheter device according to the invention.
Figure 3:
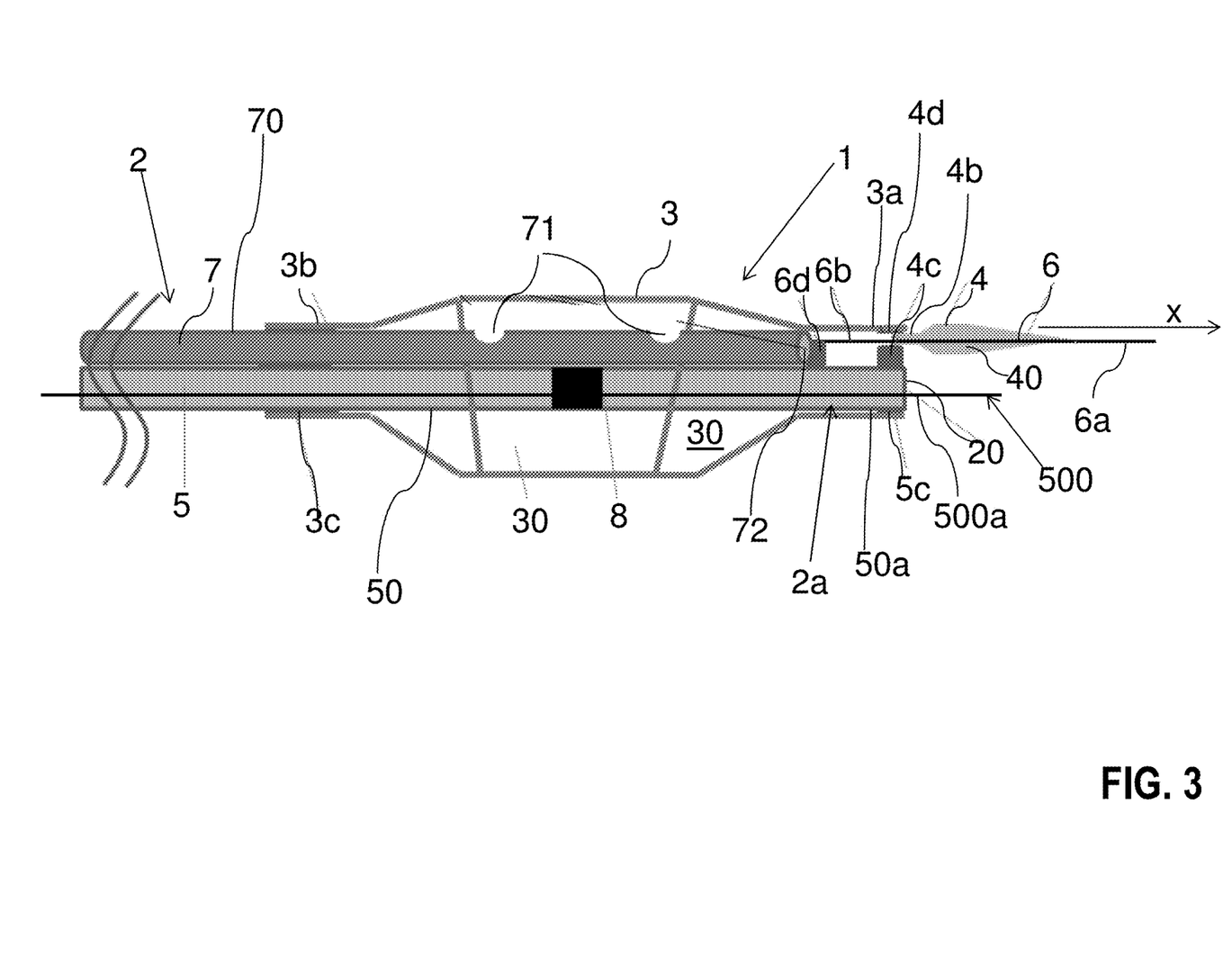
FIG. 3 shows a schematic sectional view of a further embodiment of a catheter device according to the invention.

FIGS. 1 to 3 show embodiments of a catheter device 1 according to the invention for the recanalisation of an occlusion O in a vessel G (see FIGS. 6(A) to 6(M)). The catheter device, according to these figures, has a catheter shaft 2, which extends along a longitudinal axis x and which has a distal end portion 2a, at which there is arranged a proximal balloon 3 for anchoring the catheter shaft 2 in the vessel G, which balloon is also configured to open the occlusion O, wherein the proximal balloon 3 has a balloon interior 30, into which a fluid medium (for example physiological saline solution, contrast agent) can be introduced in order to expand the proximal balloon 3. The catheter device 1 furthermore has a distal balloon 4 arranged at the distal end portion 2a for opening the occlusion O initially, wherein the distal balloon 4 likewise has a balloon interior 40, into which a fluid medium (for example physiological saline solution, contrast agent) can be introduced in order to expand the distal balloon 4. The device 1 furthermore has a guide wire lumen 5 formed by the catheter shaft 2 and a guide wire 500, which can be guided in the guide wire lumen 5, wherein the catheter shaft 2, at the distal end portion 2a, has an opening 20, via which the guide wire 500 can be guided out from the guide wire lumen 5 and from the catheter shaft 2.

It is provided in accordance with the invention that the opening 20 is arranged such that the guide wire 500 extends outside the distal balloon 4 by a portion 500a of the guide wire 500 guided out from the guide wire lumen 5 via the opening 20, and in so doing can be introduced in particular past the distal balloon into the occlusion, in order to guide the catheter shaft 2 to the target location.

In particular, the opening 20 is arranged along the longitudinal axis x of the catheter shaft 2 between a distal end 3a of the proximal balloon and a proximal end 4b of the distal balloon 4.

The guide wire 500 for example may have a diameter of 0.36 mm, wherein the inner diameter of the guide wire lumen 5 is larger, such that the guide wire 500 can slide easily in the guide wire lumen 5.

In order to introduce or position the distal balloon 4 in the occlusion O, the catheter device 1 preferably has an elongate guide element 6, which is formed separately from the guide wire 500 and which in particular is visible under x-ray and protrudes with a distal end portion 6a from the distal balloon 4. In accordance with an embodiment the distal end portion 6a has a length (along the longitudinal axis x) in the range of from 2 mm to 10 mm. The guide element 6 extends in particular along the longitudinal axis x through the balloon interior 40 of the distal balloon 4, wherein the distal end portion 6a of the guide element 6 is guided out from the distal balloon 4 at a distal end 4a of the distal balloon 4.

Furthermore, the wire or the guide element 6 in accordance with an embodiment may have a diameter of 0.1 mm.

Furthermore, the distal balloon 4 in accordance with an embodiment may have, at 6 atm, a diameter D2 in the range of from 1.0 mm to 2.0 mm. In this regard, it is also provided that the diameter D2 is smaller than the diameter D1 of the fully dilated or expanded proximal balloon 3.

Furthermore, the distal balloon 4 in accordance with an embodiment may have a length in the range of from 2 mm to 10 mm along the longitudinal axis x.

Furthermore, in accordance with one embodiment, twice the wall thickness of the distal balloon 4 may lie in the range of from 0.02 mm to 0.04 mm. The profile diameter of the distal balloon 4 in accordance with one embodiment (folded onto the guide element 6, which has a diameter of 0.1 mm) may be less than or equal to 0.2 mm.

Furthermore, in accordance with one embodiment the distal balloon 4 may be made of one of the following materials: polyamide, in particular PA12, polyethylene terephthalate, polyurethane or polyether block amide such as Pebax (tradename). Furthermore, the distal balloon may have a coating on its outer side which is hydrophilic or hydrophobic.

It is furthermore provided that the guide wire lumen 5 of the catheter shaft 2 is surrounded by a wall 50. In order to track the proximal balloon 3, it may furthermore be provided that the catheter device 1 has at least one x-ray marker 8, which in the balloon interior 30 of the proximal balloon 3 is arranged on a wall 50 which surrounds the guide wire lumen 5. It is furthermore provided that the wall 50 of the guide wire lumen 5 extends through the balloon interior 30 of the proximal balloon 3 along the longitudinal axis x and in so doing delimits the opening 20 in the distal end portion 2a of the catheter shaft 2 at the end face.

Furthermore, the catheter shaft according to FIGS. 1 to 3 has a shaft lumen 7, which is surrounded by a wall 70 and via which a fluid medium, for example physiological saline solution or contrast agent, can be introduced into the balloon interior 30 of the proximal balloon 3 and into the balloon interior 40 of the distal balloon 4 in order to expand the proximal and distal balloon 3, 4.

In accordance with the embodiment shown in FIG. 1 it is provided that the wall 70 of the shaft lumen 7 extends along the longitudinal axis x through the balloon interior 30 of the proximal balloon 3, wherein the shaft lumen 7 is fluidically connected to the balloon interior 40 of the distal balloon 4 or leads into the balloon interior 40, such that the distal balloon 4 can be dilated via the shaft lumen 7. In order to dilate the proximal balloon 3, the wall 70 of the shaft lumen 7 also has lateral outlet openings 71 arranged in the balloon interior 30 of the proximal balloon 3, such that the fluid medium can be introduced also into the balloon interior 30 of the proximal balloon 3 via the outlet opening 71 in order to expand the proximal balloon 3.

It is furthermore provided in accordance with FIG. 1 that a proximal end portion 6b of the guide element 6 extending through the balloon interior 40 of the distal balloon 4 is secured to the wall 70 of the shaft lumen 7 via a, for example bonded, connection 6c.

FIG. 2 by contrast shows an alternative embodiment, wherein here the wall 70 of the lumen 7 ends at the proximal end 3b of the proximal balloon or the shaft lumen 7 leads into the balloon interior 30 of the proximal balloon 3. The balloon interior 30 of the proximal balloon 3 is fluidically connected here to the balloon interior 40 of the distal balloon 4, such that the distal balloon 4 can be deleted or can be inflated via the proximal balloon 3. In the embodiment according to FIG. 2, it is provided, in contrast to FIG. 1, that the proximal end portion 6b of the guide element 6 is connected to the wall 50 of the guide wire lumen 5 via a, for example bonded, connection 6d.

FIG. 3 shows a further embodiment of a catheter device according to the invention, wherein here the wall 70 of the shaft lumen 7 likewise extends through the balloon interior 30 of the proximal balloon 3, but ends along the longitudinal axis x before the distal end 3a of the proximal balloon 3, wherein an end-side outlet opening 72 of the wall 70 faces the distal balloon 4 and is fluidically connected thereto via the circumferential distal end 3a of the proximal balloon 3. The proximal end portion 6b of the guide element/wire 6 protrudes here into the distal end 3a of the proximal balloon 3 and is connected to the wall 50 of the guide wire lumen 5 via a, for example bonded, connection 6d.

Furthermore, it is in particular provided that a proximal end 4b of the distal balloon 4 is connected on the one hand via a, for example bonded, connection 4d to the distal end 3a of the proximal balloon 3 and on the other hand via a, for example bonded, connection 4c to a distal end 50a of the wall 50 of the guide wire lumen 5. The distal end 50a of the wall 50 of the guide wire lumen may furthermore be connected via a, for example bonded, connection 5c to the distal end 3a of the proximal balloon 3. Lastly, in particular the proximal end 3b of the proximal balloon 3 is connected via a, for example, bonded connection 3c to the shaft 2 or the wall 50 of the guide wire lumen and/or the wall 70 of the shaft lumen 7.

Figure 4:
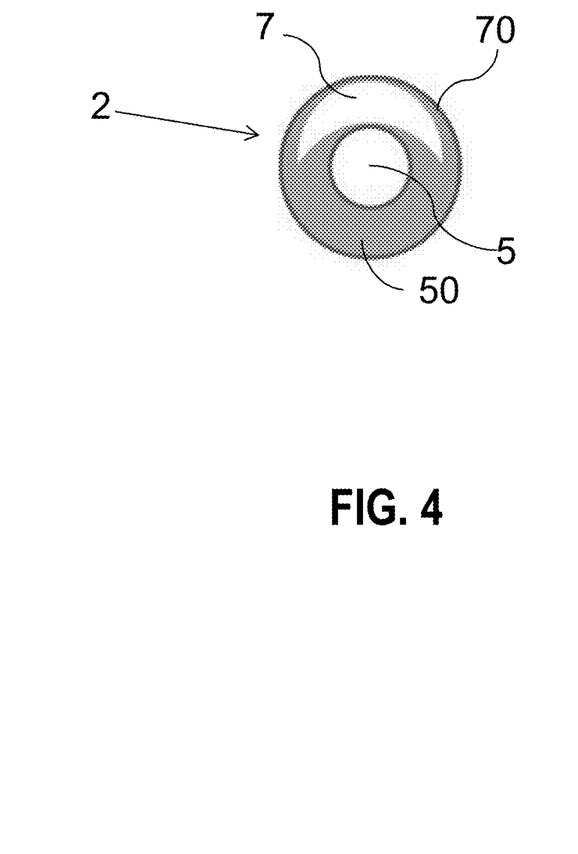
FIG. 4 shows a sectional depiction of an embodiment of the catheter shaft of the catheter device.
Figure 5:
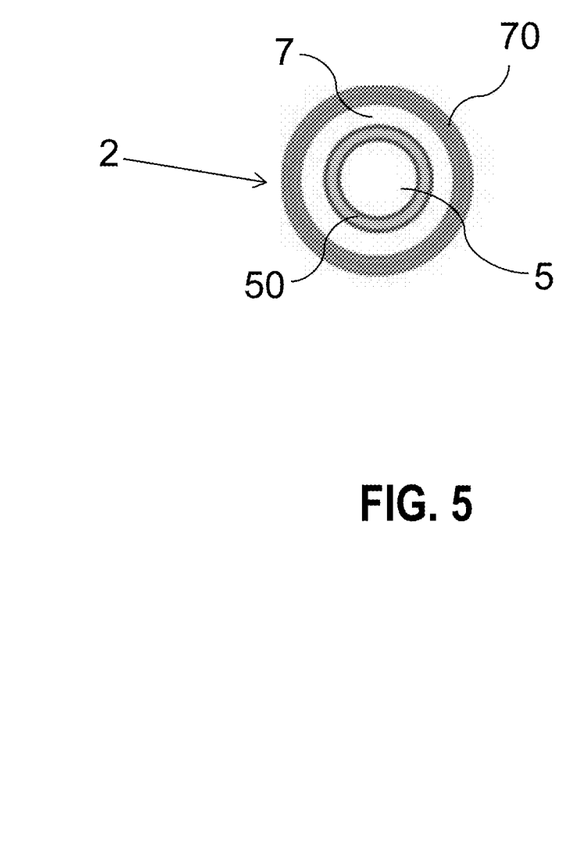
FIG. 5 shows a sectional depiction of an alternative embodiment of the catheter shaft of the catheter device.

The catheter shaft 2 can surround or delimit the shaft lumen 7 or the guide wire lumen 5 in different ways. FIGS. 4 and 5 show two alternatives, which can both be used in the embodiments shown in FIGS. 1 to 3. According to FIG. 4 the guide wire lumen 5 and the shaft lumen 7 can be extended in the catheter shaft 2 adjacently, side by side. The two walls 50 and 70 are accordingly connected to one another or are formed integrally with one another along the longitudinal axis x.

Alternatively, the shaft lumen 7 and the guide wire lumen 5 can be arranged coaxially with one another according to FIG. 5, wherein the guide wire lumen 5 is surrounded by the shaft lumen 7. The wall 50 of the guide wire lumen 5 extends here in the shaft lumen 7 surrounded by the outer wall 70.

FIGS. 6A to 6M show, by way of example, the use of a catheter device 1 according to the invention (for example in the design according to FIGS. 1 to 3) for the recanalisation of a total occlusion O of a vessel G.

Figure 6A:
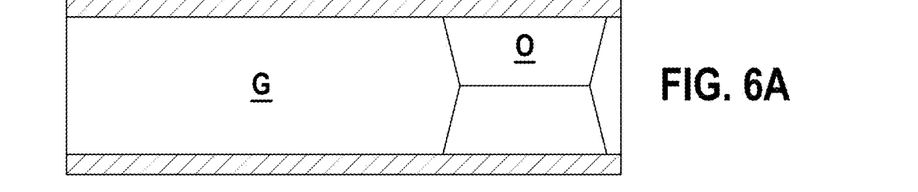
FIGS. 6A-6M shows a recanalisation of a total occlusion (CTO) with use of a catheter device according to the invention.
Figure 6B:
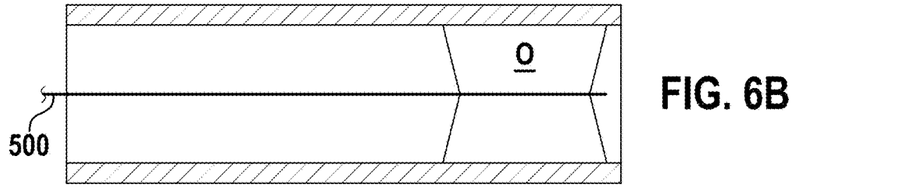
Figure 6C:
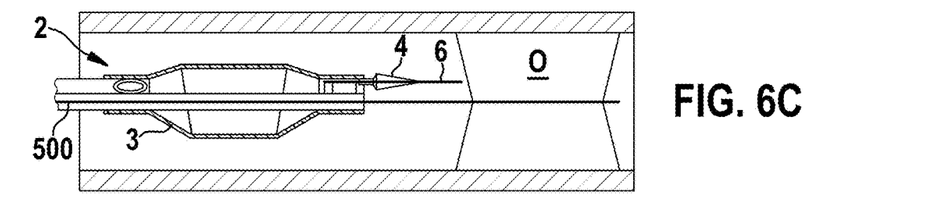
Figure 6D:
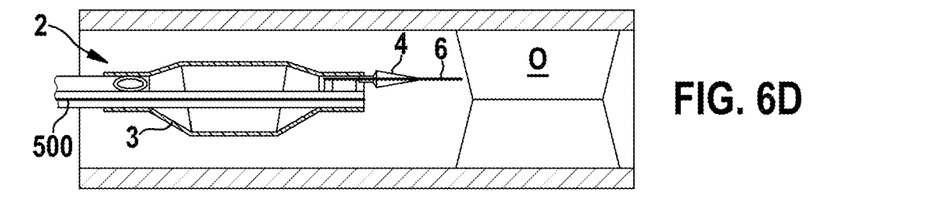
Figure 6E:
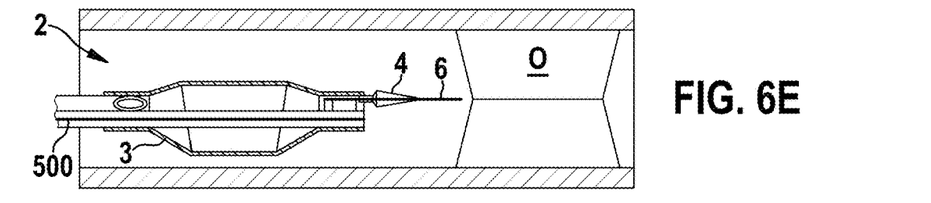

Following an initial assessment of the occlusion (CTO) O (see FIG. 6A), the guide wire 500 of the catheter device 1 is guided through the occlusion O (see FIG. 6B). The catheter shaft 2 of the device 1 is then positioned in the vessel or the artery G by the guide wire 500 (see FIG. 6C).

Figure 6F:
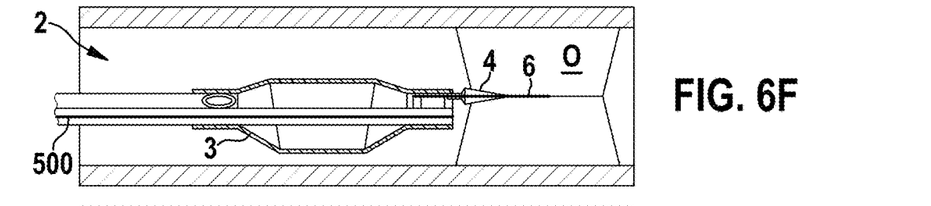

Following the positioning of the catheter shaft 2, the guide wire 500 is retracted (see FIG. 6D) and the distal balloon 4 is positioned relative to the occlusion O (see FIG. 6E) and introduced thereinto (see FIG. 6F).

Figure 6G:
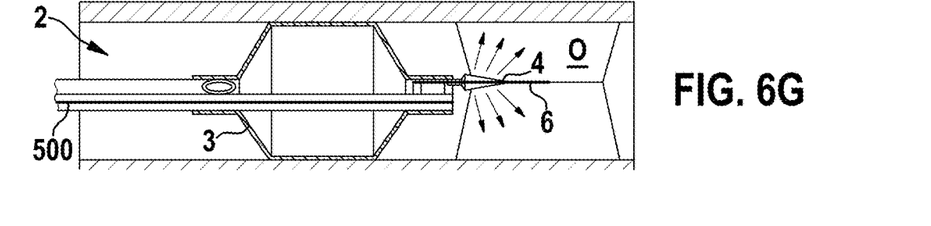

The proximal balloon 3 and the distal balloon 4 are then inflated in order to open the occlusion O (see FIG. 6G). Here, the proximal balloon 3 is used to anchor the catheter shaft 2 in the vessel G.

Figure 6H:
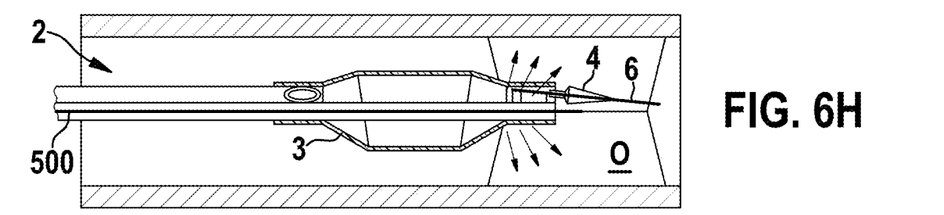
Figure 6I:
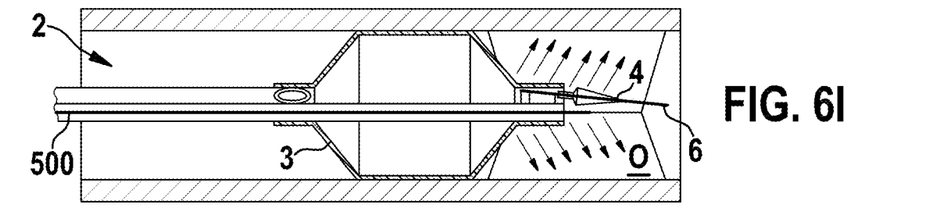

The two balloons 3, 4 are then deflated and introduced in part into the occlusion O via the guide wire 500 and the elongate guide element 6 (see FIG. 6H). The two balloons 3, 4 then dilate it, wherein the distal balloon 4 opens the occlusion O to a greater extent, and the proximal balloon 3 in turn anchors the shaft 2 in the vessel G (see FIG. 6I).

Figure 6J:
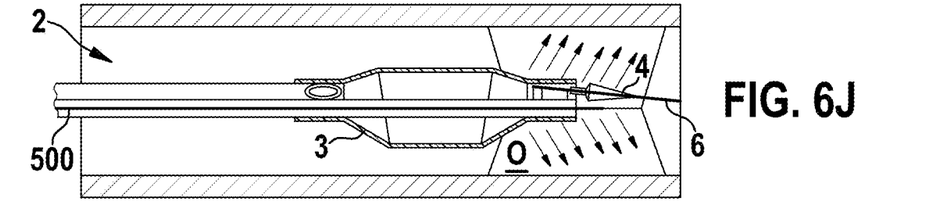
Figure 6K:
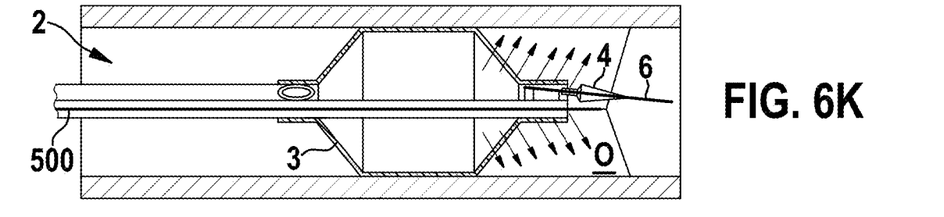

According to FIG. 6J, the two balloons 3, 4 are then deflated and introduced further into the occlusion O. The two balloons 3, 4 are then dilated again in order to open the lesion O to an even greater extent (see FIG. 6K).

Figure 6L:
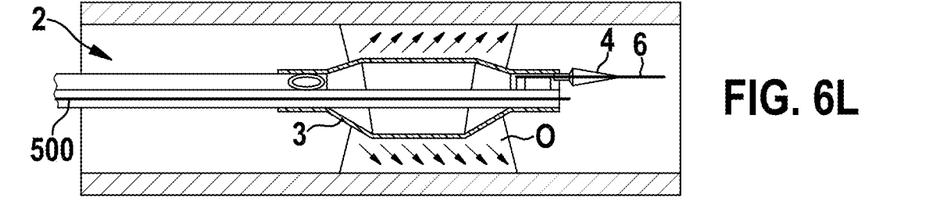
Figure 6M:
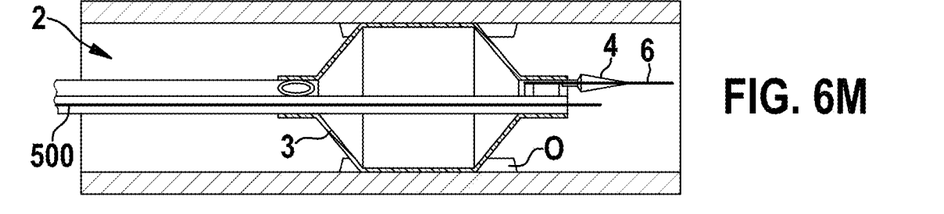

According to FIG. 6L, both balloons 3, 4 are then deflated and the proximal balloon 3 is introduced centrally into the occlusion O and then dilated (see FIG. 6M) in order to open the vessel G to the end diameter at the position of the occlusion O.

The device 1 according to the invention advantageously enables a recanalisation of a CTO by a single device 1, thus saving time during the intervention and reducing the risk for the patient accordingly.

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

What is claimed is:

1. A catheter device for recanalisation of an occlusion in a vessel, comprising:
    a catheter shaft extending along a longitudinal axis having a distal end portion,
    a proximal balloon arranged at the distal end portion, the proximal balloon being sized for anchoring the catheter shaft in the vessel and for opening the occlusion, wherein the proximal balloon has a balloon interior into which a fluid medium can be introduced to expand the proximal balloon,
    a distal balloon arranged at the distal end portion distally from the proximal balloon, the distal balloon being sized for initially opening the occlusion, wherein the distal balloon has a balloon interior into which a fluid medium can be introduced in order to expand the distal balloon, wherein a diameter of the proximal balloon transverse to the longitudinal axis of the catheter shaft in a fully expanded state is greater than a diameter of the distal balloon transverse to the longitudinal axis of the catheter shaft in a fully expanded state
    a guide wire lumen surrounded by the catheter shaft, wherein the guide wire lumen runs within and through the proximal balloon,
    a guide wire configured to be guided in the guide wire lumen,
    an elongate guide element formed separately from the guide wire having a distal end portion which protrudes from the distal balloon and
    an opening formed by the guide wire lumen at the distal end portion of the catheter shaft via which the guide wire can be guided out from the guide wire lumen and from the catheter shaft, the opening being located along the longitudinal axis of the catheter shaft between a distal end of the proximal balloon and a proximal end of the distal balloon, wherein
    the opening is arranged such that the guide wire can extend with a portion of the guide wire outside the distal balloon.

2. The catheter device according to claim 1, wherein the guide element extends through the balloon interior of the distal balloon, wherein the distal end portion of the guide element is guided out from the distal balloon at a distal end of the distal balloon.

3. The catheter device according to claim 1, wherein the guide element is formed by a wire that is visible under x-ray.

4. The catheter device according to claim 1, wherein the guide wire lumen of the catheter shaft is surrounded by a wall.

5. A catheter device for recanalisation of an occlusion in a vessel, comprising:
    a catheter shaft extending along a longitudinal axis having a distal end portion, a proximal balloon arranged at the distal end portion, the proximal balloon being sized for anchoring the catheter shall in the vessel and for opening the occlusion, wherein the proximal balloon has a balloon interior into which a fluid medium can be introduced to expand the proximal balloon, a distal baboon arranged at the distal end portion distally from the proximal balloon, the distal balloon being sized for initially opening the occlusion, wherein the distal balloon has a balloon interior into which a fluid medium can be introduced in order to expand the distal balloon, wherein a diameter of the proximal balloon transverse to the longitudinal axis of the catheter shaft in a fully expanded state is greater than a diameter of the distal balloon transverse to the longitudinal axis of the catheter shaft in a fully expanded state a guide wire lumen surrounded by the catheter shaft, a guide wire configured to be guided in the guide wire lumen, an elongate guide element formed separately from the guide wire having a distal end portion which protrudes from the distal balloon and an opening at the distal end portion of the catheter shaft via which the guide wire can be guided out from the guide wire lumen and from the catheter shaft, wherein the opening is arranged sack that the guide wire can extend with a portion of the guide wire outside the distal balloon, wherein the guide wire lumen of the catheter shaft is surrounded by a wall and the guide wire lumen extends through the balloon interior of the proximal balloon.

6. The catheter device according to claim 1, wherein the catheter shaft has a shaft lumen surrounded by a wall, the shaft lumen being configured to introduce a fluid medium into the balloon interior of the proximal balloon and into the balloon interior of the distal balloon to expand the proximal and the distal balloon.

7. The catheter device according to claim 6, wherein the shaft lumen leads into the balloon interior of the proximal balloon, and the balloon interior of the distal balloon is fluidically connected to the shaft lumen via the balloon interior of the proximal balloon.

8. The catheter device according to claim 6, wherein the wall of the shaft lumen extends through the balloon interior of the proximal balloon, the shaft lumen is fluidically connected to the balloon interior of the distal balloon, and the wall of the shaft lumen has at least one lateral outlet opening arranged in the balloon interior of the proximal balloon, via which outlet opening a fluid medium can be introduced into the balloon interior of the proximal balloon to expand the proximal balloon.

9. The catheter device according to claim 1, wherein a proximal end portion of the guide element is connected to a wall of the shaft lumen.

10. The catheter device according to claim 1, wherein a proximal end portion of the guide element is connected to a wall of the guide wire lumen.

11. The catheter device according to claim 1, wherein the shaft lumen and the guide wire lumen extend adjacently in the catheter shaft.

12. A catheter device for recanalisation of an occlusion in a vessel, comprising:

a catheter shaft extending along a longitudinal axis having a distal end portion, a proximal balloon arranged at the distal end portion, the proximal balloon being sized for anchoring the catheter shall in the vessel and for opening the occlusion, wherein the proximal balloon has a balloon interior into which a fluid medium can be introduced to expand the proximal balloon, a distal baboon arranged at the distal end portion distally from the proximal balloon, the distal balloon being sized for initially opening the occlusion, wherein the distal balloon has a balloon interior into which a fluid medium can be introduced in order to expand the distal balloon, wherein a diameter of the proximal balloon transverse to the longitudinal axis of the catheter shaft in a fully expanded state is greater than a diameter of the distal balloon transverse to the longitudinal axis of the catheter shaft in a fully expanded state a guide wire lumen surrounded by the catheter shaft, a guide wire configured to be guided in the guide wire lumen, an elongate guide element formed separately from the guide wire having a distal end portion which protrudes from the distal balloon and an opening at the distal end portion of the catheter shaft via which the guide wire can be guided out from the guide wire lumen and from the catheter shaft, wherein the opening is arranged such that the guide wire can extend with a portion of the guide wire outside the distal balloon, wherein the shaft lumen and the guide wire lumen are arranged coaxially with one another, wherein the guide wire lumen is surrounded by the shaft lumen.

13. The catheter device according to claim 1, comprising at least one x-ray marker arranged in the balloon interior of the proximal balloon on a wall of the guide wire lumen.

14. The catheter device according to claim 1, wherein the diameter of the proximal balloon in the fully expanded state is at least twice as big as the diameter of the distal balloon in the fully expanded state.

15. The catheter device according to claim 14, wherein the diameter of the proximal balloon in the fully expanded state is more than 10-times as big as the diameter of the distal balloon in the fully expanded state.

16. The catheter device according to claim 14, wherein the distal balloon is more rigid than the proximal balloon.

\* \* \* \* \*